US005466227A

United States Patent [19]
Kessenich

[11] Patent Number: 5,466,227
[45] Date of Patent: Nov. 14, 1995

[54] PATIENT CONTROLLED ANALGESIC INJECTOR ASSEMBLY AND METHOD OF ASSEMBLING SAME TO AN INFUSER UNIT

[75] Inventor: Peter Kessenich, Waukegan, Ill.

[73] Assignee: Abbott Laboratories, Abbott Park, Ill.

[21] Appl. No.: 179,295

[22] Filed: Jan. 10, 1994

[51] Int. Cl.[6] .................................................. A61M 37/00
[52] U.S. Cl. ........................................................ 604/246
[58] Field of Search .................................... 604/246, 201, 604/85, 263, 406, 56, 82–88, 91, 92, 411–414, 201, 205, 206

[56] References Cited

U.S. PATENT DOCUMENTS

| | | | |
|---|---|---|---|
| 4,578,064 | 3/1986 | Sarnoff et al. | 604/201 |
| 4,828,551 | 5/1989 | Gertler et al. | 604/236 |
| 4,850,978 | 7/1989 | Dudar et al. | 604/201 |
| 4,936,829 | 6/1990 | Zdeb et al. | 604/85 |
| 5,049,129 | 9/1991 | Zdeb et al. | 604/85 |

*Primary Examiner*—C. Fred Rosenbaum
*Assistant Examiner*—Manuel Mendez
*Attorney, Agent, or Firm*—A. Nicholas Trausch, III

[57] ABSTRACT

An injector assembly and method are provided for assembling the injector assembly to a patient controlled analgesic infuser unit. The injector assembly is provided in one-piece and includes an injector element having first and second portions with a cannula extending therebetween. The first portion is configured for connection to a stopper of a vial containing an analgesic where the connection enables the analgesic to flow out of the vial and through the cannula to the second portion of the injector element upon advancement of the stopper and the connected injector element within the vial by the infuser unit. A drug administration set is permanently connected to the second portion of the injector element for receiving the analgesic from the cannula. After the vial is emptied, the empty vial can be removed from the injector element and a full vial readily can be connected to the injector element without having to provide an additional injector element and disconnect and re-connect the drug administration set from the injector element. This type of injector assembly reduces changeover time, the risk of contamination and needle sticks and the amount of non-recyclable waste and storage space required as a result of eliminating replacement of the injector element each time a vial is replaced.

9 Claims, 2 Drawing Sheets

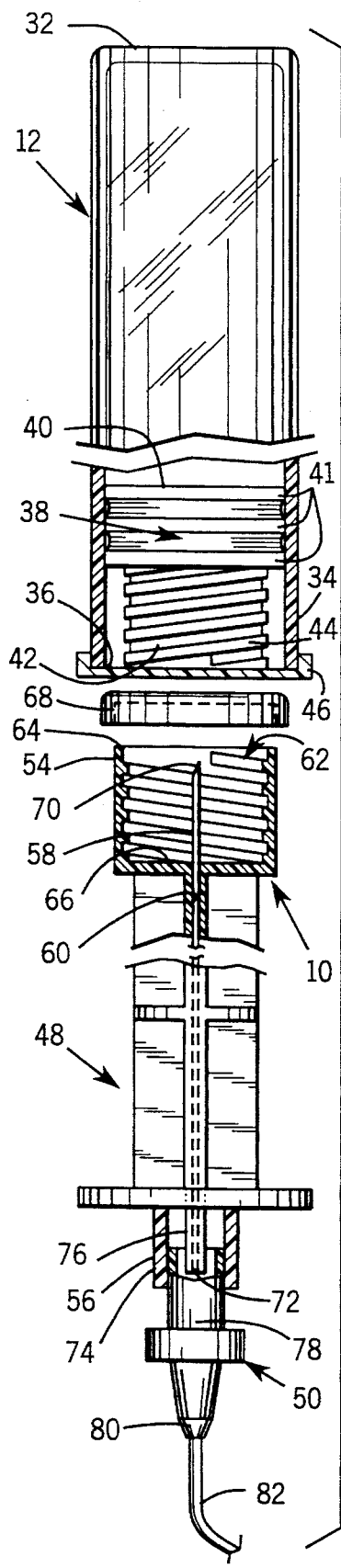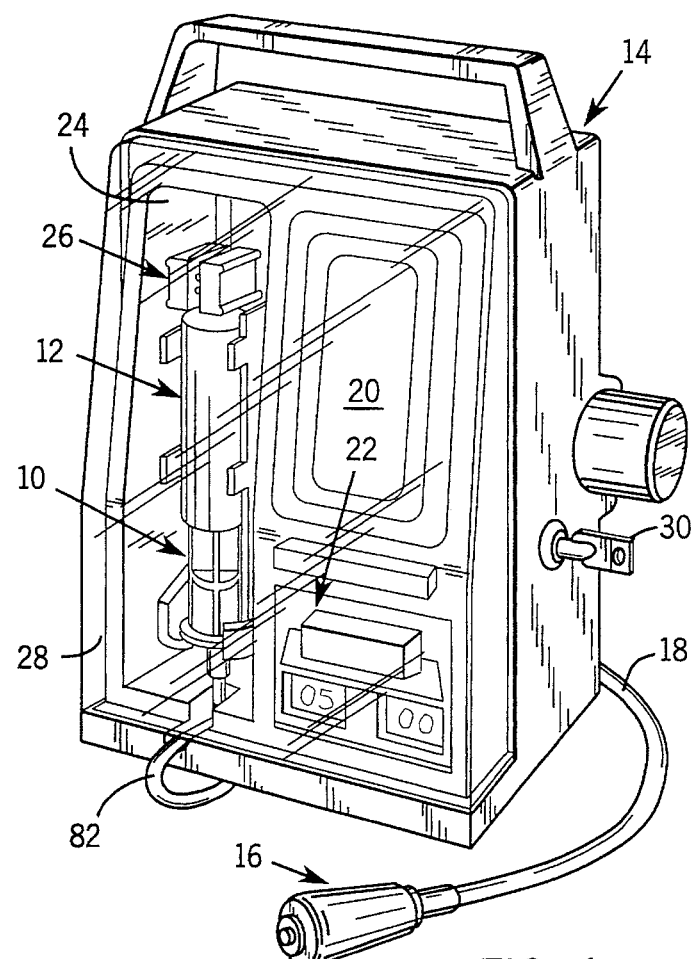
FIG. 2
FIG. 1

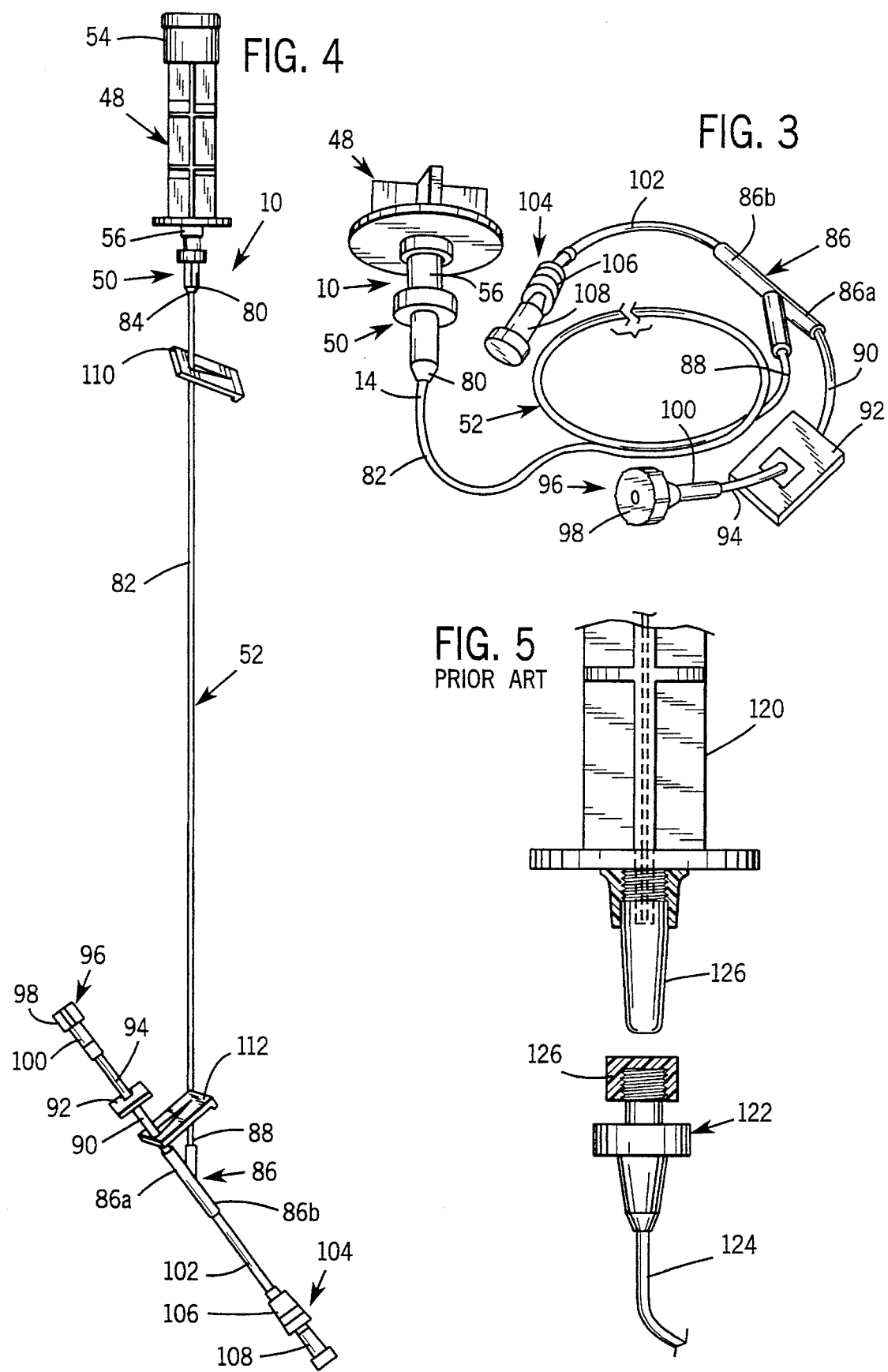

PATIENT CONTROLLED ANALGESIC INJECTOR ASSEMBLY AND METHOD OF ASSEMBLING SAME TO AN INFUSER UNIT

TECHNICAL FIELD

The present invention relates generally to patient controlled analgesia or PCA systems, and more particularly, to a one-piece analgesic injector assembly and method of assembling the injector assembly to a PCA infuser unit. The injector assembly preferably includes an injector element for operable communication with a vial containing an analgesic and a drug administration set having an anti-siphon valve which is permanently connected to the injector element. Such an injector assembly reduces the time required for replacing vials at the point of use, the risk of contamination and needle sticks, the amount of non-recyclable waste and storage space and the risk of an accidental overdose from improperly positioned or damaged parts which can occur during assembly of a drug administration set to the injector element at the point of use.

BACKGROUND OF THE INVENTION

PCA systems typically include an electronic infuser unit which can be readily activated by a patient to enable the patient to directly administer an analgesic in a prescribed dosage and within a predetermined time period. The infuser unit accepts a vial having a desired analgesic sealed therein and an injector element which are activated by the infuser unit to dispense the analgesic in the prescribed dosage from the vial to a drug administration set in communication with the injector element.

The drug administration set typically includes an anti-siphon valve at one end that is manually connected to the injector element at the point of use. Other portions of the drug administration set are manually connected to an intravenous administration set and a venipuncture device for administration of the analgesic into the blood stream of the patient.

Such systems typically include a vial having an opening sealed by a stopper or plunger and a sealing cap which encloses the stopper within the vial to maintain the sterility of the plunger and vial before use. The injector element includes a metal cannula which extends between first and second opposite ends where the portion of the cannula proximate the first end pierces the stopper upon threaded engagement therewith. Both the first and second ends of the injector element also include sealing caps to prevent contamination of the cannula and reduce the risk of the cannula accidentally "sticking" an attendant before or during assembly.

FIG. 5 illustrates a prior art injector element having a sealing cap on its second end and positioned for threaded engagement with an anti-siphon valve of a drug administration set. The anti-siphon valve also includes a protective cap to reduce contamination of the anti-siphon valve and the microbore administration set before use.

In these existing PCA systems, both the vial and the injector element are provided in the same sterile package while the anti-siphon valve and drug administration set are provided in a separate sterile package. Accordingly, when a vial is emptied during use, the vial and injector element first are removed from the infuser unit, the injector element is manually disconnected from the anti-siphon valve and the empty valve and associated injector element are removed from the infuser unit and discarded as non-recyclable waste.

A new package containing a full vial and a new injector element then is retrieved from stock, the protective covers from the vial and both ends of the injector element are removed and the injector element is threadedly connected to the stopper of the vial. The anti-siphon valve then is threadedly connected to the injector element and the vial and injector element are connected to the infuser unit.

A disadvantage of these existing PCA systems is that the anti-siphon valve must be disconnected from the used injector element and re-attached to a new injector element each time the vial is emptied. This not only increases costs by having to provide a new injector element each time a vial is replaced, but also requires additional installation time. Such systems also increase the risk of contamination by breaking open the established sterile system as well as the risk of an accidental overdose by an improper connection.

Additionally, the risk of a needle stick to the patient or the attendant exists from handling the injector element while trying to connect the rather small anti-siphon valve to the injector element. This work typically is done at the bedside of a patient which sometimes does not afford ample room or proper lighting making the work difficult.

Furthermore, since the injector element includes a cannula, it cannot be recycled. Thus, replacement of an injector element each time the vial needs replaced substantially increases the quantity of non-recyclable waste.

Finally, since both the vial and injector element are replaced when the vial is empty, storage must be provided for both of these items. Storage areas in hospitals and other treatment centers is at a premium, especially for drugs which have additional security, refrigeration or other requirements, such as an analgesic, particularly a controlled substance such as morphine.

It therefore would be desirable to provide a one-piece injector assembly for use with a vial which preferably includes an anti-siphon valve permanently connected to both an injector element and a drug administration set. Such an injector assembly would enable an attendant to merely remove an empty vial from the injector element and install a full vial to the injector element without removing the anti-siphon valve or drug administration set from the injector element.

Since the anti-siphon valve does not need to be disconnected and re-attached to the injector element, costs and assembly time are significantly decreased which are major goals in the health care industry. Additionally, the risk of contamination and a needle stick is reduced since the only connection necessary is the relatively easy threaded connection between the vial stopper and the injector element.

Furthermore, since such an injector assembly does not require a new injector element each time the vial is replaced, the amount of non-recyclable waste is reduced by approximately 60% which provides a distinct environmental advantage. This similarly provides a reduction in the amount of storage space required for injector elements by approximately 60%.

Additionally, since the manual connection between the anti-siphon valve and the injector element is eliminated, the risk of improper connection or breaking of these elements is reduced, thereby reducing the possibility of an accidental overdose.

The present invention provides an injector assembly and method of installing the injector assembly to an infuser unit which can accommodate the above-discussed benefits and features.

SUMMARY OF THE INVENTION

The invention provides an injector assembly and method of assembling the injector assembly to a PCA infuser unit where the injector assembly is provided in one-piece for use with a vial containing a desired drug. The vial and injector assembly are configured for operable communication with the PCA infuser unit which enables a patient to administer a prescribed quantity of drug when desired, rather than having to wait for an attendant to provide such a drug.

In a preferred form of the injector assembly, an injector element is provided having first and second portions with a cannula extending therebetween. The first portion of the injector element is configured for connection to a vial stopper which enables the drug to flow out of the vial through the stopper and the cannula upon connection of the injector element thereto.

An anti-siphon valve is permanently connected to the second portion of the injector element for receiving the drug from the cannula and preventing siphoning of the drug out of the vial. A drug administration set is permanently connected to the anti-siphon valve for receiving the drug from the anti-siphon valve and delivering the drug to a patient.

Accordingly, when a vial is emptied, only the vial and stopper need to be replaced, not the injector element. This significantly reduces the changeover time, risk of contamination, needle sticks and the amount of non-recyclable waste and storage space required as a result of eliminating replacement of the injector element each time a vial is replaced.

In a preferred form of the method, a PCA infuser unit and a vial containing an analgesic and an aperture sealed by a stopper movable within the vial are provided. A one-piece injector assembly is connected to the stopper by an injector element including first and second portions with a cannula extending therebetween. An anti-siphon valve is permanently connected to the second portion of the injector element with a drug administration set permanently connected to the anti-siphon valve.

The stopper is pierced with the cannula during connection of the injector element with the stopper to provide a flow of the analgesic from the vial through the stopper and the cannula to the anti-siphon valve and the drug administration set. The drug administration set then is connected to an intravenous gravity administration set and a venipuncture device for injection into the blood stream of a patient. The vial and injector element then are connected to the infuser unit for activation by a patient when desired to provide a prescribed amount of analgesic from the vial into the patient's blood stream.

Numerous other advantages and features of the present invention will become readily apparent from the following description of the invention, the claims and the accompanying drawings.

BRIEF DESCRIPTION OF THE DRAWINGS

FIG. 1 is a perspective view of a PCA infuser unit typically utilized with a vial and the injector assembly of the invention which are illustrated connected thereto;

FIG. 2 is an exploded view, in partial section, of a vial and the injector assembly of the invention;

FIG. 3 is a bottom perspective view of an injector assembly of the invention illustrating the permanently connected anti-siphon valve and drug administration set;

FIG. 4 is an elevational view of the permanently connected one-piece injector assembly of the invention; and FIG. 5 is an exploded view, in partial section, of a prior art injector element and discrete anti-siphon valve along with the protective caps typically provided with these elements.

DESCRIPTION OF THE PREFERRED EMBODIMENTS

While this invention is susceptible of embodiment in many different forms, this specification and the accompanying drawings disclose only one specific form as an example of the invention. The invention is not intended to be limited to the embodiment described, the scope of the invention being pointed out in the appended claims.

For ease of description, the assembly of this invention is described in the normal, upright, operating position and terms such as upper, lower, horizontal etc. are utilized with reference to this position. It will be understood, however, that the apparatus of this invention may be manufactured, stored, transported, and sold in an orientation other than the position described.

Some of the figures illustrating the embodiment of the assembly of the present invention show conventional components, structural details and mechanical elements that will be recognized by one skilled in the art. The detailed descriptions of such elements, however, are not necessary to an understanding of the invention and, accordingly, are not presented herein.

Referring to FIGS. 1 and 2, an injector assembly of the present invention is generally designated by the reference numeral 10. The injector assembly 10 preferably is utilized with a vial 12 and a Patient Controlled Analgesia or PCA infuser unit 14, generally illustrated in FIG. 1.

The infuser unit 14 accepts the injector assembly 10 and the vial 12 and activates the vial 12 and injector assembly 10 upon demand by a patient to dispense a prescribed dose of drug, preferably an analgesic, within a given time period. Such infuser units 14 are sold in the U.S.A. by Abbott Laboratories, Inc., One Abbott Park Road, Abbott Park, Ill. 60064-3500 under the name LIFECARE® PCA INFUSER as part of the LIFECARE® PCA brand patient controlled analgesic administration system.

The infuser unit 14 preferably is powered by one or more rechargeable batteries or battery packs (not illustrated), but can be powered from an electrical outlet if desired. The infuser unit 14 preferably is positioned at the bedside of a patient and typically is mounted to a pole utilized with intravenous gravity administration sets (not illustrated). Alternatively, the infuser unit 14 can be mounted to a wall, placed on a table or positioned in any other desired way and can be designed as a portable device, if desired.

To enable a patient to activate the infuser unit 14 when desired, the infuser unit 14 includes an activation button or switch 16 connected to the infuser unit 14 through an electrical cable 18. The length of the cable 18 can vary and enables the patient to activate the infuser unit 14 from a remote location, such as from bed.

The infuser unit 14 includes a display panel 20 which provides an attendant with a variety of information. The information preferably provided by the display panel 20 can include the volume of drug delivered, the lockout interval which must elapse before subsequent patient-initiated doses are permitted, the total number of doses, the battery status, whether an occlusion exists and whether the syringe needs checking. It is to be understood, however, that the information provided by the display panel 20 can vary.

A control panel 22 also is provided on the infuser unit 14 as well as a recess 24 including a mounting and activation mechanism 26. The mechanism 26 mounts the vial 12 and a portion of the injector assembly 10 within the recess 24 and provides a flow of drug out of the vial 12 to the injector assembly 10 when desired.

To prevent tampering with the control panel 22, the vial 12, injector assembly 10 or any other portion of the infuser unit 14, a cover 28 is mounted to the front of the infuser unit 14. The cover 28 preferably is secured by a key 30 and is clear so that an operator can examine the vial 12, the display panel 20 and the control panel 22 without removing the cover 28. Additionally, to alert an attendant of any tampering of the infuser unit 14, one or more alarms (not illustrated) can be included.

As FIG. 2 illustrates, the vial 12 preferably is made of glass and is tubular in shape having a first closed end 32 and a second end 34 which is defined by an aperture 36. A stopper member 38 is positioned within the vial 12 to seal off the aperture 36 and prevent a desired drug within the vial 12 from being emitted from the vial 12 until pierced by the injector assembly 10 as described below.

The stopper 38 preferably is made from a substantially flexible material such as flexible plastic or rubber and is designed for sliding, sealing engagement within the vial 12, similar to a syringe. The stopper 38 includes a first end 40 and a plurality of sealing ridges 41 about its periphery proximate the first end 40. The stopper 38 also includes a second end 42 with threads 44 about its periphery proximate the second end 42.

The sealing ridges 41 enable the sealing, sliding movement of the stopper 38 within the vial 12 while the threads 44 enable attachment of the injector assembly 10 as described below. The number, size and shape of sealing ridges 41 and threads 44 can vary so long as they function as described herein.

To protect and maintain the sterility of the vial 12 during shipping, storage and handling, the stopper 38 is positioned for shipment with both ends 40 and 42 being completely inside the vial 12. A protective cap 46 then is attached over the aperture 36 with the stopper 38 captured within the vial 12.

In order to funnel drug out of the vial 12 and through the stopper 38 when pierced, the first end 40 of the stopper 38 is conically tapered toward a first central recess (not illustrated). To assist in piercing the stopper 38 by the injector assembly 10, the second end 42 of the stopper 38 includes a second central recess (not illustrated).

The first and second recesses substantially are in alignment and extend a predetermined distance within the stopper 38 but do not intersect. Accordingly, a small amount of material of the stopper 38 remains between the first and second recesses which is pierced by the injector assembly 10.

AS FIGS. 2, 3 and 4 illustrate, the injector assembly 10 preferably is provided in one-piece and includes an injector element 48, an anti-siphon valve 50 and a drug administration set 52. The injector element 48 preferably is formed from plastic and includes first and second opposite end portions 54 and 56 and a metal cannula 58. The cannula 58 extends through and is mounted within a channel 60 which extends between the first and second end portions 54 and 56 of the injector element 48. An anti-siphon valve 50 is generally a one-way, pressure activated valve. Anti-siphon valves are commonly known and used in IV fluid administration. For example, anti-siphon valves are disclosed in U.S. Pat. Nos. 3,889,710, 4,286,628, and 4,535,820.

As FIG. 2 illustrates, in order to connect the injector element 48 to the stopper 38, the first end portion 54 of the injector element 48 includes a threaded recess 62 for threaded connection with the threads 44 of the second end 42 of the stopper 38. The recess 62 has a first open end 64 and a second substantially closed end 66 through which the channel 60 and cannula 58 extend. To protect and maintain the sterility of the injector element 48 and cannula 58 during shipping, storage and handling, the first open end 64 of the recess 62 preferably is covered with a protective cap 68.

The cannula 58 includes first and second opposite ends 70 and 72. The first end 70 extends a predetermined distance within the recess 62 of the injector element 48 for piercing the stopper 38 upon threaded engagement of the injector element 48 with the stopper 38. Once the stopper 38 is pierced, the drug within the vial 12 can flow into the cannula 58 and through the injector assembly 10 as described in detail below.

To reduce the risk of an attendant acquiring a "stick" from the first end 70 of the cannula 58, the first end 70 of the cannula 58 is positioned a slight distance from the first open end 64 of the recess 62. To assist in piercing the stopper 38, the first end 70 of the cannula 58 is tapered to a point.

In order to permanently connect the anti-siphon valve 50 to the second end 56 of the injector element 48 as described below, the second end 56 includes a first outer sleeve 74. To protect the second end 72 of the cannula 58 during connection of the anti-siphon valve 50 and enable a flow of drug therebetween, the second end 56 of the injector element 48 also includes a second inner sleeve 76 positioned within the confines of the first outer sleeve 74.

The anti-siphon valve 50 preferably is made of plastic and prevents unwanted siphoning of drug from the vial 12. The anti-siphon valve 50 includes a first end 78 for permanent connection with the outer sleeve 74 of the injector element 48 and a second end 80 for permanent connection with the drug administration set 52. The first end 78 is configured to fit snugly within the confines of the outer sleeve 74 so that is can be permanently attached thereto, preferably by heat staking.

A variety of other methods also can be utilized for permanently attaching the first end 78 of the anti-siphon valve 50 to the outer sleeve 74 of the injector element such as sonic welding, shrink banding, R.F. welding, induction heating, U.V. cured adhesive, adhesives, bonding, solvent bonding, mechanical attachment, insert molding and spin welding, electromagnetic bonding, vibration welding, hot-gas welding and hot-plate welding. It is to be understood, however, that the connection between the anti-siphon valve 50 and the injector element 48 can vary so long as it is substantially permanent as described herein.

As FIGS. 3 and 4 illustrate, the drug administration or PCA set 52 substantially includes a first piece of tubing 82 having a first end 84 permanently connected to the second end 80 of the anti-siphon valve 50, such as by one of the methods described above or any other method. The drug administration set 52 preferably is relatively small in size and can be a mini-bore or micro-bore type administration set.

The drug administration set 52 conveys the drug from the cannula 58 of the injector element 48 to the blood stream of a patient through the use of a venipuncture device and an intravenous or I.V. gravity administration set (not illustrated). In order to readily connect the I.V. set to the tubing 82, a "Y" connector 86 is provided on a second end 88 of the first piece of tubing 82.

One branch 86a of the "Y" connector 86 includes a second piece of tubing 90 connected thereto which terminates in a check valve 92. A third piece of tubing 94 is connected to the check valve 92 and terminates in a connector 96 for the I.V. set. The connector 96 preferably includes a non-vented, threaded luer lock cap 98 and a luer lock female adaptor 100. It is to be understood, however, that the particular arrangement of the connection between the "Y" connector 86 and the I.V. set can vary so long as it enables the desired attachment as described herein.

Another branch 86b of the "Y" connector 86 includes a fourth piece of tubing 102 connected thereto which terminates in a connector 104 for connection to the venipuncture device. If desired, the connector 104 can include a locking spin collar 106 and a male adaptor and air filter assembly 108.

As FIG. 4 illustrates, to shut-off or regulate the flow of fluid through the first and second pieces of tubing 82 and 90, slide clamps 110 and 112 can be positioned respectively thereon. The slide clamps 110 and 112 primarily are utilized to assist in priming the system, but also can completely block the flow of fluid if desired.

To assemble the injector assembly 10 to the vial 12 and infuser unit 14, a vial 12, which is separately packaged, is obtained from stock along with an injector assembly 10, which likewise is separately packaged. Using aseptic techniques, the packages are opened to remove the vial 12 and the injector assembly 10 and the protective caps 46 and 68 are removed from the vial 12 and injector element 48, respectively.

The open end 64 of the injector element 48 then is inserted within the aperture 36 of the vial 12 and is threadedly engaged with the stopper 38 by rotating the injector element 48 clockwise. As the threads 44 of the stopper 38 engage the threaded recess 62 of the injector element 48, the pointed first end 70 of the metal cannula 58 engages and begins to pierce the stopper 38 proximate a central axis of the stopper 38.

Once the injector element 48 is completely threaded to the stopper 38, the first end 70 of the cannula 58 completely pierces the material between the first and second recesses of the stopper 38. At this point, the cannula 58 is exposed to the drug within the vial 12.

Before connecting the drug administration set 52 to the I.V. set or the venipuncture device, the cannula 58 and the drug administration set 52 first must be "primed" to remove the air therein. This is accomplished by advancing the injector element 48 and connected stopper 38 within the vial 12 until the air is purged out of the drug administration set 52 by the drug. The slide clamp 110 then is closed.

After priming the I.V. set in a similar manner, the slide clamp 112 is opened and the female adaptor 100 of the connector 96 is attached to the I.V. set. The lower portion or fourth tube 102 of the drug administration set 52 then is primed with I.V. solution, which is temporarily stopped after priming the fourth tube 102 by closing a slide clamp on the I.V. set (not illustrated.)

The connector 104 then is attached to the venipuncture device which must be primed with I.V. solution if not already indwelling. If a locking feature is desired, the male adaptor 108 is attached to the venipuncture device and the spin collar 106 is advanced to engage the threads of the venipuncture device. If a locking feature is not needed, the spin collar 106 can be positioned along the fourth tube 104 at a position away from the male adaptor 108.

The clamp on the I.V. set then is re-opened and adjusted to the proper flow rate. The slide clamp 110 is opened at this point to enable the drug to flow into the patient.

The vial 12 and injector element 48 then are inserted within the recess 24 of the infuser unit 14 and mounted to the activation mechanism 26 with the first tube 82 of the drug administration set 52 extending out of a bottom of the recess 24 as illustrated in FIG. 1. An attendant then provides the proper settings on the control panel 22 and the cover 28 is positioned over the face of the infuser unit 14 and locked in place with the key 30. The infuser unit 14 then can be activated when desired by a patient by depressing button 16 to dispense the prescribed quantity of drug in the proper intervals.

FIG. 5 illustrates a prior art injector element 120 and discrete anti-siphon valve 122 and associated drug administration set 124. Since the anti-siphon valve 122 is not permanently attached to the injector element 120, both the injector element 120 and the anti-siphon valve 122 must include caps 126 to maintain the sterility of those elements during shipping and handling.

Accordingly, when assembling these elements at the point of use, the caps 126 first must be removed and the rather small connection between the anti-siphon valve 122 and the ejector element 120 must be accomplished. Extreme care must be taken when connecting these element to avoid a "stick" from the cannula and since an improper or broken connection could result in an accidental overdose.

In contrast, the present invention overcomes this problem by permanently attaching the anti-siphon valve 50 to the injector element 48 at the factory. This not only eliminates the need for any caps, such as caps 126 of the prior art device, but reduces assembly time at the point of use, maintains the sterility of the injector assembly 10 and eliminates the risk of an improper or broken connection between the injector element 48 and the anti-siphon valve 50.

Additionally, with the present invention only one injector element 48 is utilized per drug administration set 52 as opposed to the prior art device which must provide a new injector element 120 with each new vial 12. With an average patient usage of three drug vials 12, substantial savings in material costs alone are obtained since the caps 126 are eliminated and the number of injector elements 48 or 120 are reduced by two thirds.

Additionally, since the injector element 48 or 120 includes a cannula, it cannot be recycled and must be properly disposed. By reducing the number of injector elements 48 used per patient, substantial cost savings in solid waste disposal are obtained.

Furthermore, since the vial 12 typically contains a prescription drug, it must be stored in a secure area, sometimes with refrigeration or other requirements. Such storage areas for what are known as "class #2 drugs" are at a premium in hospitals and other treatment facilities. Accordingly, since the vial 12 of the present invention can be packaged separately from the injector element 48, approximately a 60% reduction in the required storage space is provided with the present invention.

It will readily be apparent from the foregoing detailed description of the invention and from the illustrations thereof that numerous variations and modifications may be effected without departing from the true spirit and scope of the novel concepts or principles of this invention.

What is claimed is:

1. A one-piece injector assembly for use with a replaceable vial having an open end and a closed end, the open end sealed by a slidable stopper, the vial containing a desired drug for controlled administration by an infuser unit, said injector assembly comprising:

a reusable injector element having first and second portions thereof with a cannula extending therebetween, said first portion having a threaded recess for threaded connection with complimentary threads on said slidable stopper of the vial, the connection between said first portion of said injector element and said stopper causing the cannula to piece said stopper so as to cause the drug to flow out of the vial through said stopper and said cannula from said first portion to said second portion upon advancement of said injector element and said stopper within the vial by the infuser unit; and a drug administration set permanently connected to said second portion of said reusable injector element for receiving the drug from said cannula so that after the stopper has been advanced from the open end of the vial to the closed end of the vial the empty vial can be removed from said injector element and a full vial can be connected to said injector element without having to provide an additional injector element and disconnect and re-connect said drug administration set from said injector element thereby reducing changeover time, the risk of contamination, the risk of a needle stick and the amount of non-recyclable waste and storage space as a result of eliminating replacement of said injector element each time a vial is replaced.

2. The injector assembly in accordance with claim 1 wherein said drug administration set includes a one-way pressure activated anti-siphon valve for preventing siphoning of drug from the vial.

3. The injector assembly in accordance with claim 1 including a one-way, pressure activated anti-siphon valve permanently connected to said second end of said injector element for preventing siphoning of drug from the vial, said drug administration set being permanently connected to said anti-siphon valve.

4. The injector assembly in accordance with claim 1 wherein said drug administration set includes a one-way, pressure activated anti-siphon valve and at least a first connection for an intravenous gravity administration set as well as a second connection for a venipuncture device.

5. An analgesic delivery assembly for use with a patient controlled analgesic infuser unit which enables a patient to directly initiate, achieve and maintain an analgesic state by allowing the patient to administer a prescribed dose of analgesic within a given time period, the infuser unit accepting and activating the delivery assembly upon demand by a patient, the delivery assembly comprising:

a replaceable vial containing a predetermined amount of a desired analgesic therein, said vial having one aperture and an opposite closed end;

a stopper member positioned within said aperture for sealing said aperture and preventing said analgesic from being emitted from said vial, said stopper being movable within said vial to the closed end;

a reusable injector element which readily can be releasible connected to said stopper for operable communication therewith, said injector element including a first portion having a threaded recess for threaded connection with complementary threads on said stopper, a second portion and a cannula extending between said first and second portions, said cannula piercing said stopper upon connection therewith and providing a flow of analgesic between said vial to said second portion upon advancement of said stopper and said injector element within said vial by said infuser unit; and an analgesic administration set permanently connected to said second portion of said injector element, said administration set including one-way, pressure activated anti-siphon valve and connections to both an intravenous gravity administration set and a venipuncture device.

6. A method of assembling a vial and a one-piece injector assembly to a patient controlled analgesic infuser unit comprising the steps of:

(a) providing a patient controlled analgesic infuser unit capable of accepting the vial and the one-piece injector assembly therein and being activated by a patient to dispense a prescribed dosage of analgesic from said vial into said injector assembly within a given time period;

(b) providing a vial containing a predetermined amount of an analgesic therein and at least one aperture sealed by a stopper member which is movable within said vial;

(c) connecting a one-piece injector assembly to said stopper member, said injector assembly including an injector element having first and second portions with a cannula extending therebetween, said first portion being connected to said stopper member and said second portion having an anti-siphon valve permanently connected thereto, said anti-siphon valve being permanently connected to at least a drug administration set;

(d) piercing said stopper with an end of said cannula positioned proximate said first portion of said injector element during connection of said injector assembly with said stopper to provide a flow of said analgesic from said vial through said stopper, said cannula and said anti-siphon valve and into said drug administration set;

(e) connecting said drug administration set to an intravenous gravity administration set and a venipuncture device which is secured to a patient to provide a flow of drug to the patient therethrough; and (f) connecting said vial and said injector element to said patient controlled analgesic infuser unit so that the patient can activate said infuser unit upon demand to provide a prescribed amount of analgesic from said vial into the patient's blood stream.

7. The method in accordance with claim 6 including priming said drug administration set prior to attaching said venipuncture device thereto.

8. The method in accordance with claim 6 including before said connecting of step (c), removing sealing caps from said vial aperture and said first portion of said injector element.

9. The method in accordance with claim 6 including after said vial is empty, removing said vial and said injector element from said infuser unit, removing said vial from said injector element, connecting a full vial to said injector element including piercing said stopper with an end of said cannula and connecting said vial and injector element to said infuser unit.

* * * * *